United States Patent [19]

Dessau

[11] Patent Number: 5,292,980
[45] Date of Patent: Mar. 8, 1994

[54] BASE-CATALYZED REACTIONS USING ZEOLITE CATALYSTS

[75] Inventor: Ralph M. Dessau, Edison, N.J.

[73] Assignee: Mobil Oil Corporation, Fairfax, Va.

[21] Appl. No.: 686,957

[22] Filed: Apr. 18, 1991

Related U.S. Application Data

[62] Division of Ser. No. 811,198, Dec. 20, 1985, Pat. No. 5,026,919.

[51] Int. Cl.$^5$ .......................... C07C 5/23; C07C 5/27
[52] U.S. Cl. .................................... 585/666; 585/664; 585/671
[58] Field of Search ................... 585/407, 666, 671

[56] References Cited

U.S. PATENT DOCUMENTS

| | | | |
|---|---|---|---|
| 3,644,200 | 2/1972 | Young | 585/666 |
| 3,697,616 | 10/1972 | McDonough et al. | 585/666 |
| 3,702,886 | 11/1972 | Argauer et al. | 423/328 |
| 3,804,746 | 4/1974 | Chu | 585/666 |
| 4,005,147 | 1/1977 | Fischer et al. | 260/593 R |
| 4,035,395 | 7/1977 | Stetter et al. | 260/347.5 |
| 4,115,424 | 9/1978 | Unland et al. | 252/432 |
| 4,170,609 | 10/1979 | Turner | 260/586 C |
| 4,215,076 | 7/1980 | Stueben et al. | 568/461 |
| 4,309,281 | 1/1982 | Dessau | 208/310 Z |
| 4,339,606 | 7/1982 | Huang et al. | 568/396 |
| 4,699,708 | 10/1987 | Dessau | 208/111 |

OTHER PUBLICATIONS

House, "Modern Synthetic Reactions", Second Edition, pp. 632–647.
Isaor, Chem Abst, vol. 77, #87756n (1972).
Calame et al, Chem Abst, vol. 80, 3172v, 1974.
Frilette et al, "Catalysis by Crystalline Aluminosilicates ... Index", J. of Catal, vol. 67, No. 1, (1981).
Pines et al, "Base Catalyzed Reactions . . . Compounds", pp. 26–27 and 498–499 (1977).

*Primary Examiner*—Asok Pal
*Assistant Examiner*—P. Achutamurthy
*Attorney, Agent, or Firm*—Alexander J. McKillop; Malcolm D. Keen; Marina V. Schneller

[57] ABSTRACT

Basic intermediate or large pore zeolites having a Constraint Index less than 12 are useful as catalysts in the dehydrogenation-aromatization of cyclic dienes, in the isomerization of olefins and in the aldol condensation, and particularly in the cyclization of acetonylacetone to 3-methyl-2-cyclopenten-1-one.

3 Claims, No Drawings

BASE-CATALYZED REACTIONS USING ZEOLITE CATALYSTS

This is a division of copending application Ser. No. 06/811,198 filed on Dec. 20, 1985, now U.S. Pat. No. 5,026,919.

BACKGROUND OF THE INVENTION

1. Field of the Invention

This invention relates to a process for effecting base-catalyzed reactions, such as aldol condensations and cyclizations, and the dehydrogenation, aromatization and isomerization of olefins using a basic zeolite as the catalyst.

2. Discussion of the Prior Art

The aldol condensation is an old and well known base-catalyzed reaction extensively described in the chemical literature and widely used to prepare a variety of compounds having industrial utility. The condensation is typified by the reaction of acetaldehyde with itself to form beta-hydroxybutyraldehyde when heated in a solution containing a base. Beta-hydroxybutyraldehyde, on further heating and/or when treated with acid, forms crotonaldehyde, due to the propensity of beta-hydroxy carbonyl compounds to eliminate water. The first step in the condensation is the formation of an enolate anion by removal of a hydrogen alpha to the carbonyl group in an acetaldehyde molecule:

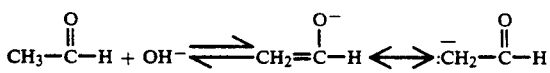

The second resonance form of the enolate anion adds to the carbonyl group of another molecule of acetaldehyde:

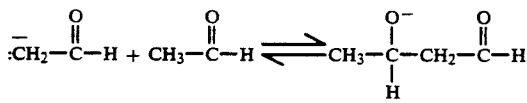

Beta-hydroxybutyraldehyde is formed when the adduct combines with a proton. It is important to note that both enolate formation and addition are equilibrium reactions.

Other aldehydes and ketones having a hydrogen alpha to the carbonyl group and capable of forming an enolate anion react in a similar fashion. For example, the aldol condensation of ketones is typified by the reaction of acetone with itself to form diacetone alcohol, and then, on dehydration, mesityl oxide.

It is not necessary that an aldehyde or ketone react with itself or that the carbonyl compound to which the anion adds also contain an alpha hydrogen atom. For example, acetone reacts readily with formaldehyde, which lacks an alpha hydrogen. Thus, it is possible to have mixed aldol condensations:
(a) aldehyde to another aldehyde;
(b) ketone to another ketone;
(c) aldehyde to ketone;
(d) ketone to aldehyde.
If both carbonyl reactants have alpha hydrogens, it is apparent that two different enolate anions can be formed and a mixture of products may result. The amount of each product formed will depend on the equilibrium constants and rates of reaction for the anion-forming and addition steps.

It is also possible for a compound having two carbonyl groups to undergo an internal aldol condensation and cyclize. For example, when a solution of gamma-diketone containing a base is heated, a cyclopenten-1-one is produced.

Aldol condensations are generally effected in an aqueous and/or alcoholic solvent in the presence of a base, such as sodium hydroxide. The overall course of the reaction and yield of product obtained depends on the equilibrium constants and rates of reaction for the intermediate steps involved. The product is generally isolated by a series of steps involving acidification of the reaction mixture, extraction with a water-immiscible non-polar solvent, separation of the aqueous and organic layers, drying of the organic layer, and distillation to recover the product.

Other base-catalyzed reactions are described in the book titled "*Base-Catalyzed Reactions of Hydrocarbons and Related Compounds*", authored by Herman Pines and Wayne M. Stalick, Academic Press New York, 1977. For example, the base-catalyzed dehydrogenation and aromatization of dienes is discussed at pages 498 and 499; alkali metal amides and alkali metal naphthalenes are disclosed as catalysts for the conversion of cyclohexadienes to benzene. The isomerization of olefins, particularly 1-enes to 2-enes, is discussed at pages 26 and 27; metal amides, metal hydrides, organoalkali metal compounds, alkali metals supported on inert carrier materials, metal hydroxides and metal oxides are stated as having shown activity as catalysts for the isomerization of olefins.

SUMMARY OF THE INVENTION

It has been discovered that certain base-catalyzed reactions can be effected in a convenient manner using a basic, shape-selective zeolite as the catalyst.

In one specific aspect, the present invention is a process for the dehydrogenation and aromatization of a cyclic diene which comprises using a basic, intermediate or large pore size zeolite, having a Constraint Index less than 12, as the catalyst.

In another specific aspect, the present invention is a process for the isomerization of an olefin which comprises using a basic, intermediate or large pore size zeolite, having a Constraint Index less than 12, as the catalyst.

In yet another specific aspect, the present invention is the improvement in a process comprising an aldol condensation which comprises using a basic, intermediate or large pore size zeolite, having a Constraint Index less than 12, as the catalyst. And in a somewhat more specific aspect, the present invention is the improvement in a process wherein a carbonyl compound having a hydrogen alpha to the carbonyl group is condensed with the same or another carbonyl compound, which comprises using a basic, intermediate or large pore size zeolite, having a Constraint Index less than 12, as the catalyst.

DETAILED DESCRIPTION OF THE INVENTION

Diene Reactants

Particularly suitable for use as reactants in the dehydrogenation-aromatization aspect of the present invention are the cyclic dienes, such as 1, 3-cyclohexadiene and 1,4-cyclohexadiene, which form benzene or a benzenoid compound.

Olefin Reactants

Particularly suitable for use as reactants in the olefin-isomerization aspect of the present invention are 1-enes of the formula $R-CH=CH_2$ wherein R is a lower alkyl group, having 1 to 4 carbon atoms, such as methyl, ethyl, propyl, isopropyl, butyl, isobutyl and sec-butyl.

Carbonyl Reactants

Suitable carbonyl compounds for use as reactants in practicing the aldol reaction aspect of the present invention are aldehydes of the formula $R_2CHCHO$ and ketones of the formula $RCOCHR_2$, having a hydrogen alpha to the carbonyl group wherein each R, individually selected, can be hydrogen, a lower-alkyl group or a phenyl group. Particularly preferred alkyl groups are lower-alkyl groups having 1 to 4 carbon atoms, such as methyl, ethyl, propyl, isopropyl, butyl, isobutyl and sec-butyl. The phenyl group may bear non-interfering substituents (substituents which do not interfere with the condensation reaction), such as lower-alkyl, halo, lower-alkoxy, etc. When the carbonyl reactant is a gamma- or delta-dicarbonyl compound, the aldol condensation can be internal and a cyclic compound would be formed. Aldehyde and ketone carbonyl compounds, as well as olefins, are described in the chemical literature, and methods for their preparation are well known to those skilled in the art.

Catalysts

The catalysts useful in practicing the process of the present invention are intermediate or large pore size zeolites, having a Constraint Index of less than 12, generally ranging downward from 12 to 0.3. Particularly preferred are intermediate pore size zeolites having a Constraint Index between about 2 to 12. These zeolites retain a degree of crystallinity for long periods of time, even when exposed to steam at high temperature, under conditions which would induce irreversible collapse of the framework of other zeolites, such as those of the X and A type. When reactivating these catalysts, relatively higher temperatures may be utilized to burn off the carbonaceous deposits formed during use.

An important characteristic of the crystal structure of intermediate or large pore zeolite catalysts is that they provide constrained access to, and egress from, the intracrystalline free space by virtue of having a pore dimension greater than about 5 Angstroms and pore windows of about a size such as would be provided by 10- or 12-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. The preferred zeolite catalysts useful in practicing the process of this invention have a silica-to-alumina mole ratio of at least about 12, and generally higher, in addition to a structure providing constrained access to the crystalline-free space. Only a minimal amount of alumina need be present.

The silica-to-alumina ratio referred to above may be determined by conventional analysis, and the ratio is meant to represent, as closely as possible, the ratio in the rigid anionic framework of the zeolite crystal and to exclude aluminum in the binder or in cationic or other form within the channels.

A simple determination of the "Constraint Index" may be made by continuously passing a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° and 950° F. (between 288° and 510° F.) to give an overall hydrocarbon conversion during the test between 10 and 60%. The mixture of hydrocarbons is passed at 1 liquid hourly space velocity (i.e., 1 volume of liquid hydrocarbon per volume of zeolite per hour) over the zeolite with a helium dilution to give a helium-to-total hydrocarbon mole ratio of 4:1. After 20 minutes on stream, a sample of the effluent is taken and analyzed, most conveniently by gas chromatography, to determine the fraction remaining unconverted, i.e., uncracked, for each of the two hydrocarbons.

The "Constraint Index" is calculated as follows:

$$\text{Constraint Index} = \frac{\log_{10} \text{(fraction of n-hexane remaining)}}{\log_{10} \text{(fraction of 3-methyl pentane remaining)}}$$

It approximates the ratio of the cracking rate constants for the two hydrocarbons.

Constraint Index (CI) values for some typical zeolites are:

| Zeolite | CI |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.8 |
| ZSM-14 | 0.5 |
| H-Zeolon | 0.4 |

It is to be understood that the above Constraint Index values typically characterize the specified zeolites, but that such are the cumulative result of several variables used in determination and calculation thereof. Thus, for a given zeolite, depending on the temperatures employed within the aforenoted range of 550° to 950° F. (288°-510° C.) with hydrocarbon conversion being between 10 and 60%, the Constraint Index may vary somewhat from that shown in the Table. Likewise, other variables, such as the crystal size of the zeolite, the presence of possible occluded contaminants and binders intimately combined with the zeolite, may affect the Constraint Index. It will, accordingly, be understood by those skilled in the art that the Constraint Index, as utilized herein, while affording a highly useful means for characterizing the zeolites of interest, is approximate, taking into consideration the manner of its determination, with probability, in some instances, of compounding variables extremes.

The class of zeolites defined herein is exemplified by ZSM-5, ZSM-11, ZSM-12, ZSM-35, ZSM-38 and other similar materials. ZSM-5 is more particularly described in U.S. Pat. No. 3,702,886. ZSM-11 is more particularly described in U.S. Pat. No. 3,832,449. ZSM-35 is more particularly described in U.S. Pat. No. 4,016,245. ZSM-38 is more particularly described in U.S. Pat. No. 4,046,859.

When prepared using conventional hydrothermal procedures, by crystallization in the presence of an organic template in a strongly alkaline solution containing an alkali metal hydroxide, and calcined to remove the organic template, the calcined crystalline zeolite formed generally contains excess alkali metal ions. The calcined zeolite can also be reacted with alkali metal or alkaline earth metal ions at basic pH's to incorporate such metal ions, and the amount of metal ions present can be modified, i.e., decreased or exchanged, by conventional cation-exchange techniques to replace alkali metal ion with hydrogen or to exchange one metal ion for another metal ion.

The basic zeolite catalysts useful in practicing the process of the present invention contain alkali metal or alkaline earth metal ions of Group I and II in excess, in molar terms, of that of the framework aluminum content. The molar excess should preferably be greater than 5 milliequivalents per 100 grams of zeolite catalyst of alkali metal or alkaline earth metal ions, such as sodium, potassium, cesium, rubidium, calcium or magnesium.

As used herein, the term zeolite catalyst is to be broadly construed. It is inclusive of crystalline aluminosilicates and aluminosilicate-like materials, provided they have the properties discussed above, particularly large or intermediate pore size and a Constraint Index of less than 12. By way of non-limiting illustration, the aluminosilicate may be an aluminoborosilicate or include in its framework oxides of other metals, such as gallium, indium, chromium, iron or the like.

Natural zeolites may sometimes be converted to basic zeolite catalyst useful in practicing the process of the present invention by one or more of various activation procedures and other treatments, such as base-exchange, steaming, alumina extraction and calcination. Natural minerals which may be so treated include ferrierite, brewsterite, stilbite, dachiardite, espistilbite, heulandite, and clinoptilolite. A convenient approach for making basic zeolites suitable for use in practicing the process of the present invention is to treat dealuminized zeolites, dealuminized using acid or steam, with cations of Group I or Group II metals. However, the preferred crystalline aluminosilicates for use in the process of the present invention are ZSM-5, ZSM-11, ZSM-12, ZSM-35, and ZSM-38, with ZSM-5 particularly preferred. Particularly preferred are highly siliceous forms of zeolite ZSM-5, such as described in U.S. Pat. No. 4,468,475.

In practicing the condensation process of the invention, it may be desirable to incorporate the above-described crystalline aluminosilicate zeolite or aluminosilicate-like material in another material resistant to the temperature and other conditions employed in the process. Such matrix materials include synthetic or naturally-occurring substances, such as clays, silica and/or metal oxides. The latter may be either naturally-occurring or in the form of gelatinous precipitates or gels, including mixtures of silica and metal oxides. Naturally-occurring clays which can be composited with the zeolite include those of the montmorillonite and kaolin familites, which families include the sub-bentonites and the kaolins, commonly known as Dixie, McNamee-Georgia and Florida clays, or others in which the main mineral constituent is halosite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia. The matrix may be in the form of a co-gel. The relative proportions of zeolite component and inorganic oxide gel matrix may vary widely, with the zeolite content ranging from between about 50 to about 99 wt %, and more, usually in the range of about 75 to 80 wt %, of the composite.

Process Conditions

Optimal yields are obtained when the reactant, usually admixed with a carrier gas, such as hydrogen or nitrogen, is passed over the zeolite catalyst or through a bed of the catalyst at a temperature in the range about 150° to 500° C. (302°–932° F.), with temperatures in the range of 200° to 450° C. (392°–842° F.) being preferred. At temperatures below about 150° C. (302° F.), the rate of reaction becomes impractically slow. On the other hand, the rate of reaction at temperatures approaching 500° C. (932° F.) will be very rapid, requiring only a very brief contact time between the reactants and the zeolite catalyst to achieve equilibrium, but decomposition or polymerization reactions affecting catalyst activity become more troublesome at temperatures above about 500° C. (932° F.). As will be apparent, the temperature selected will depend in part on the activities of the reactants and the catalyst utilized, and the time the reactants remain in contact with the catalyst. Effecting the reaction at a temperature in the range of about 350° to 450° C. (662°–842° F.) provides rapid equilibrium with minimal risk of the reactants or products being decomposed. It is important to note that no significant amount of condensation occurs at such temperatures in the absence of a catalyst.

When effecting reactions of the type described on a commercial or manufacturing scale, the product is separated and unconverted reactant, mixed with fresh reactant, is passed to the reactor. Such recycle of reactant gives an overall high rate of conversion.

The invention is further illustrated by means of the following non-limiting examples, in which all percentages are by weight, unless the contrary is stated. In the experimental procedure described, condensation was affected in a downflow gas reactor containing the basic zeolite catalyst. The reactant carbonyl compound was fed by means of a Sage syringe pump in a stream of a carrier gas. The reactor effluent was collected in a chilled vessel and then analyzed on a 12 meter 3% SE-30 capillary column at 60° C. (140° F.). The reactants and products were identified by comparison of retention times on two different columns with those of authentic samples, and by GC-MS analysis on a Hewlett-Packard 5992 instrument.

EXAMPLE 1

This example illustrates the aldol condensation of an aldehyde.

Employing hydrogen as the carrier gas, vaporized acetaldehyde was passed through a reactor packed with ZSM-5 zeolite having a silica-to-alumina ratio of 26,000 to 1 and an Na content of 1.48%. About 20% of the acetaldehyde fed was converted to crotonaldehyde per pass at temperatures in the range of 170° to 247° C. (338°–477° F.). Use of a solid catalyst avoids the isolation procedures required when the reaction is effected in solution.

EXAMPLE 2

This example illustrates the aldol condensation of a ketone.

Acetone, first percolated through a bed of alumina, was passed through a reactor containing 0.54 g of ZSM-5 zeolite having a silica-to-alumina ratio of 26,000 to 1 and an Na content of 1.48%. No condensation products were observed at reaction temperatures below 200° C. (392° F.). When the reactor containing zeolite was heated to 280° to 370° C. (536°–698° F.), about 10% of the acetone fed was converted to mesityl oxide. Some phorone was also formed.

EXAMPLE 3

This example illustrates an aldol condensation using a mixture of aldehydes as the reactants.

Using the catalyst and the procedure described in the previous examples, an equimolar mixture of ortho- and para-tolualdehyde with acetaldehyde was fed to the reactor containing the ZSM-5 zeolite at 400° to 450° C. (752°–842° F.). The exiting gas stream contained 13.6% crotonaldehyde, 3.3% para-methylcinnamaldehyde and 1.9% ortho-methylcinnamaldehyde.

EXAMPLE 4

This example illustrates an internal aldol condensation and the formation of 3-methyl-2-cyclopenten-1-one.

Acetonylacetone 1.2 ml/hour in nitrogen was passed through a reactor containing ZSM-5 zeolite having a silica-to-alumina ratio of 26,000 to 1 and an Na content of 1.48%. At 350° C. (662° F.), a 92.6% yield of 3-methyl-2-cyclopenten-1-one was obtained.

In another experiment, acetonylacetone was passed through a ZSM-5 zeolite having a silica-to-alumina ratio of 600 to 1. An 89.1% yield of 3-methyl-2-cyclopenten-1-one was obtained at 350° C. (662° F.).

In another experiment, acetonylacetone was passed through a ZSM-11 zeolite having a silica-to-alumina ratio of 4600 to 1 and a Na content of 1%. Again operating at 350° C. (662° F.), the yield of 3-methyl-2-cyclopenten-1-one was 90.6%.

Such high yields per pass are attributed to the stability of the ring system formed. Thus, the process of the present invention provides a particularly convenient procedure for the preparation of 3-methyl-2-cyclopenten-1-one.

EXAMPLE 5

This example illustrates use of a basic zeolite to dehydrogenate and aromatize a cyclic diene.

1,3-Cyclohexadiene, supplied from a room temperature varporizer, was passed over 1 g of calcined ZSM-5 catalyst having a silica-to-alumina-ratio of 600 to 1 and an Na content of 1.0% at a temperature of 400° C. (752° F.). The cyclohexadiene was contained in a stream of hydrogen flowing at the rate of 50 ml/min. The reactor effluent contained 16.2% benzene, 1.2% cyclohexene and 23.6% 1,4-cyclohexadiene; 59% of unreacted 1,3-cyclohexadiene was recovered.

When 1,3-cyclohexadiene was passed through the reactor under similar conditions, but in the absence of the zeolite catalyst, no conversion of the diene to benzene was observed.

It is noted that the prior art processes using strong bases, such as alkali metal amides and alkali metal naphthenates, are described as disproportionation reactions, and relatively large amounts of cyclohexene are formed together with benzene. The process of the present invention using basic zeolites as the catalyst yields only minor quantities of cyclohexene relative to the amount of benzene produced.

EXAMPLE 6

This example illustrates use of a basic zeolite to isomerize an olefin.

A mixture of butene-1 (20 ml/min) and nitrogen (50 ml/min) was passed over 0.5 g of calcined ZSM-5 catalyst having a silica-to-alumina ratio of 600 to 1 and an Na content of 1.0% at a temperature of 350° C. (662° F.). The reactor effluent contained 20.1% trans-2-butene and 12.6% cis-2-butene; 67.3% butene-1 was recovered.

I claim:

1. A process for catalytically isomerizing olefins comprising contacting an olefin of the formula R—CH=CH$_2$, wherein R is an alkyl of 1 to 4 carbon atoms, with a catalyst composition comprising a zeolite, wherein the zeolite is ZSM-5 and
   wherein the catalyst composition contains ions of alkali metal or alkaline earth metal, wherein the ions are present in a molar amount which exceeds framework aluminum content of the zeolite, on a molar basis,
   wherein said contacting is undertaken under conditions effective to convert the olefin to an isomer thereof.

2. The process of claim 1, wherein there is an excess of metal ions which is greater than 5 milliequivalents per 100 grams of zeolite catalyst.

3. The process of claim 1, wherein the isomer is trans butene.

* * * * *